United States Patent [19]

Romito et al.

[11] 4,382,063
[45] May 3, 1983

[54] STERILE INDICATOR DEVICE

[75] Inventors: Vincent A. Romito, North Hollywood; Loran H. Bruso, Ontario, both of Calif.

[73] Assignee: Parke-Davis Company, Morris Plaines, N.J.

[21] Appl. No.: 380,978

[22] Filed: May 24, 1982

Related U.S. Application Data

[63] Continuation of Ser. No. 73,761, Sep. 10, 1979, abandoned, which is a continuation of Ser. No. 257,782, Apr. 27, 1981, abandoned.

[51] Int. Cl.³ .................. G01N 21/78; G01N 33/00
[52] U.S. Cl. ................................ 422/57; 116/207; 374/162; 422/58; 422/87; 436/1
[58] Field of Search .................. 422/55, 56, 57, 58, 422/86, 87, 88, 119; 116/206, 207, 216; 252/408; 374/162; 436/1

[56] References Cited

U.S. PATENT DOCUMENTS

| | | | |
|---|---|---|---|
| 2,308,087 | 1/1940 | Lappala | 422/56 |
| 3,002,385 | 10/1961 | Wahl et al. | 422/119 X |
| 3,620,677 | 11/1971 | Morison | 422/56 |
| 3,684,737 | 8/1972 | Emigh | 252/408 |
| 3,862,824 | 1/1975 | Chapman | 422/56 |
| 3,975,162 | 8/1976 | Renn | 422/56 |
| 3,981,683 | 9/1976 | Larsson et al. | 116/207 X |
| 4,138,216 | 2/1979 | Larsson et al. | 422/56 |
| 4,240,926 | 12/1980 | McNeely | 23/230 R X |

Primary Examiner—Arnold Turk

[57] ABSTRACT

A sterility indicator device comprising a base of steam permeable, absorbent material, e.g. paperboard, having mounted thereon at least one, though preferably three separate indicator ink spots of chromium chloride that change color in response to predetermined combinations of time, temperature and saturated steam, impermeable transparent cover films bonded to the top surface of the base overlaying the indicator ink spots and to the bottom surface of the base thereby preventing the escape of corrosive reactants there through, and an adhesive substance, to be used to bond the impermeable cover films to the base.

6 Claims, 4 Drawing Figures

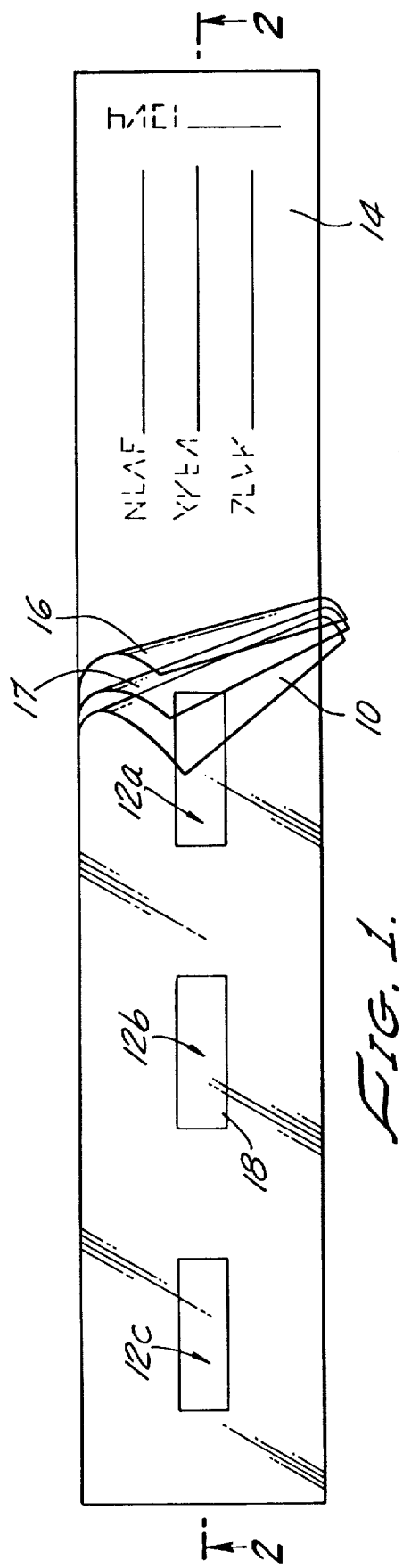
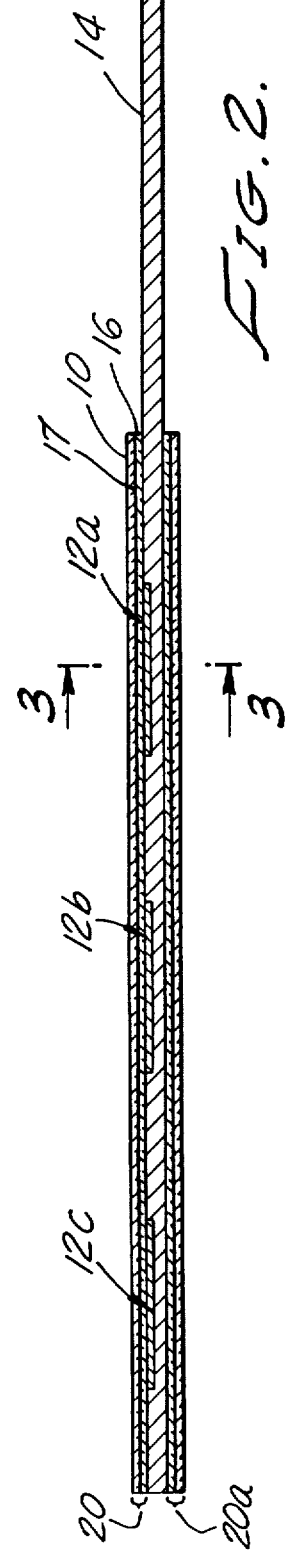
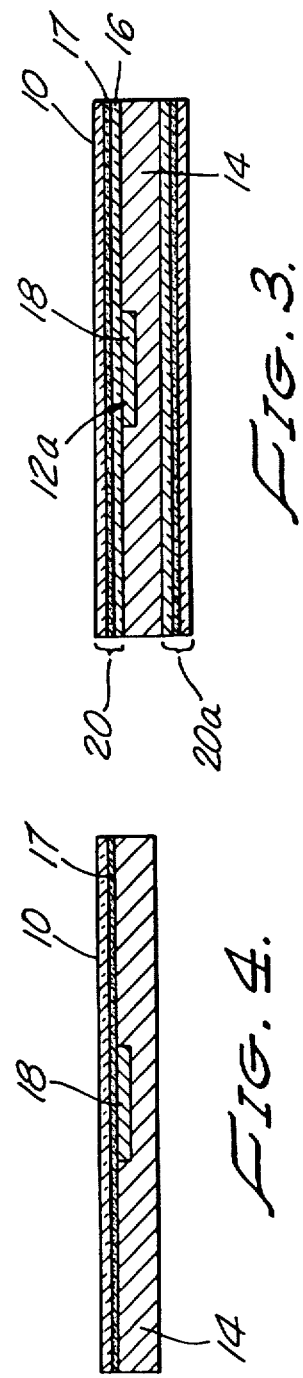
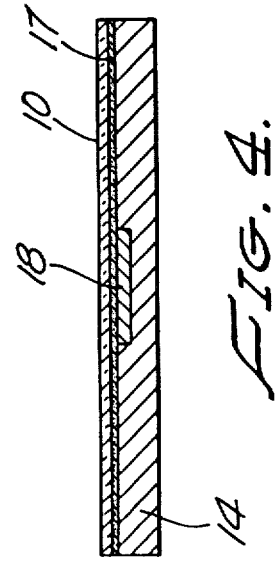

STERILE INDICATOR DEVICE

CROSS REFERENCE TO RELATED APPLICATIONS

This application is a continuation of Ser. No. 257,782, filed Apr. 27, 1981, now abandoned for a *STERILE INDICATOR DEVICE*, which application is a continuation of Ser. No. 073,761, filed Sept. 10, 1979 which has been abandoned.

BACKGROUND OF THE INVENTION

The invention relates to a sterility indicator device comprising a steam permeable base, indicator ink spots mounted thereon, an impermeable transparent cover film bonded to a substantial portion of the top surface of the base overlaying the indicator ink spots and to the bottom surface of the base.

More particularly, the present invention relates to an improved sterility indicator device which relies on time, temperature and steam to cause a color change in an indicator ink spot.

It is well known in the prior art that heat in conjunction with moisture will destroy micro organisms, a thorough discussion of which is presented in U.S. Pat. No. 3,981,683, Larsson et al, entitled *TEMPERATURE RESPONSIVE STERILITY INDICATOR*.

There have been numerous attempts by the prior art to develop chemical sterilization indicators, see for example U.S. Pat. Nos. 3,360,337, 3,652,249, and 3,341,238.

As pointed out in the Larsson Patent's discussion of the prior art, not only is the time/temperature relationship important in killing micro organisms but this relationship must also be dependent on the presence of moisture for complete sterilization. In the absence of moisture spore kill at 250°-270° F. is negligible, but in the presence of steam at these temperatures spore kill essentially complete in 2-12 minutes.

Thus for a chemical based sterility indicator to effectively indicate conditions of spore kill its function must be dependent upon time—temperature—and moisture, e.g. saturated steam.

Chemical indicator inks such as for example chromium chloride have been used in autoclaves for verifying the sterility conditions of rubber goods, instruments, basins, other nonporous materials, hospital lab clothing, bed linens, sponges and other items which may become contaminated by bacteria. The indicator inks may be formulated so as to be sensitive to particular time—temperature—and saturated steam conditions for given sterilization requirements.

A number of inks upon reacting with saturated steam during the sterilization process release corrosive reaction products which attack and damage extensively the items being sterilized. For example indicator inks formulas containing anhydrous chromium chloride ($C_rCl_3$) function as excellent indicators of time/temperature/saturated steam conditions within the autoclave, however upon reacting with saturated steam produce highly corrosive hydrochloric acid and/or chlorine gas. Substantial damage results when either the gas, the acid or both come into contact with any of the sterilized goods, particularly hospital or laboratory clothing, bed linens, and similar items constructed of naturally occurring or synthetic fibers.

Old solutions to this problem have been to contain the indicator devices in small transparent plastic holders. These holders, however, created an additional expense, were easily misplaced, cumbersome to use and did not provide the stringent quality control necessary in sterilization procedures.

The instant invention overcomes the defects of the prior art by the lamination of a clear impermeable protective covering over the indicator ink spots and the base on which the ink spots are mounted so as to contain any corrosive reaction products within the indicator preventing their contact with the sterilized goods while providing a prepackaged, easy to use reliable device for ascertaining whether sterilization conditions have been met.

It is, therefore, an object of this invention to provide a chemical sterilization indicator device which contains a steam permeable, absorbent base, indicator ink or inks mounted thereon, an impermeable transparent covering film for preventing the escape of corrosive reaction products bonded to a substantial portion of the base, and an adhesive substance for bonding the covering to the base.

It is a further object of this invention to provide a protective covering and means to adhere the covering to the base which, when exposed to autoclave sterilization, will be capable of retaining their clarity and not interfere with the visual display of the indicator device, e.g. observing the color changes of the indicator inks.

It is another object of this invention to provide a chemical sterilization indicator that will not react to dry heat but will react only when steam has been present during the sterilization process. Thus by this failure to react will warn of the presence of air in the sterilizer.

Another object of the present invention is to provide a chemical sterilization indicator which when exposed in an autoclave, will indicate whether conditions of under sterilization, correct sterilization or over sterilization have occurred.

It is still a further object of this invention to provide a chemical sterilization indicator which provides a permanent record of the time/temperature/saturated steam conditions within sterilization equipment.

BRIEF DESCRIPTION OF THE DRAWINGS

The invention will be further described as to an illustrated embodiment in conjunction with the attached drawings, in which:

FIG. 1 is a perspective view of the invention;

FIG. 2 is a longitudinal cross-sectional view of the invention;

FIG. 3 is a latitudinal cross-sectional view of the invention; and

FIG. 4 is a cross-sectional view similar to FIG. 3 but illustrating an alternative form of the invention.

DESCRIPTION OF THE PREFERRED INVENTION

As noted above, the invention provides for a particular type of chemical sterilization indicator device for use in connection with sterilization apparatus, such as, for example, a steam autoclave.

The device of the present invention is comprised of an absorbent, steam permeable base material, such as paperboard or the like, indicator ink visually responsive to a combination of factors including time, temperature and saturated steam in varying degrees, which is mounted on the base, a gas impermeable protective transparent covering bonded to and surrounding a substantial portion of the base and overlaying the indicator ink which prevents the escape of corrosive reaction products therethrough, and an adhesive to bond the covering to the base.

As a result of the device of the present invention, the risk of chemical corrosives escaping from the reacted indicator inks during the sterilization process has been virtually eliminated. In addition, the overall appearance of the indicator device has been substantially improved in comparism with the existing prior art devices.

With reference now to the drawings in detail, FIG. 1 depicts the chemical sterilization indicator of the present invention. The base is constructed of a gas/liquid permeable, and absorbent paperboard material or the like and has a generally elongated rectangular configuration.

Mounted on the base are three separate indicator ink spots 12a, 12b and 12c which undergo color changes in response to predetermined combinations of certain sterilization conditions of time, temperature and saturated steam. Indicator spot 12a will color indicate conditions representing over-sterilization; spot 12b will color indicate correct conditions of sterilization and spot 12c will color indicate conditions of understerilization, depending upon the particular combination of time, temperature and saturated steam the indicator is exposed to. The preferred embodiment utilizes anhydrous chromium chloride ($C_rCl_3$) in the chemical indicator inks, which is reactive to saturated steam at temperatures of approximately 230° F. to 280° F., the temperature range in which sterilization, e.g. thermal death of pathogenic organisms and their spores, occurs.

The chromium chloride based indicator ink spots 12a, 12b and 12c are formulated to react to a predetermined combination of time, temperature and saturated steam conditions during the sterilization process to produce a visual response, e.g. color change, due to the formation of chromium sesquichloride with the associated release of hydrochloric acid and/or chlorine gas.

As shown by FIGS. 1, 2 and 3 a substantial portion of the base material 14 containing indicator ink spots 12a, 12b and 12c is placed between two transparent covering films 10 which are impermeable to saturated steam and the corrosive reaction products produced by the reacting chromium chloride. The covering films 10, preferentially constructed of a polyester film material, are bonded to the base 14 on its top and bottom surfaces by means of an interposed film of thermoplastic material 16, such as polypropylene which when heated to its softening point acts as a adhesive. The two composite films 20 and 20a, comprised of an impermeable covering film 10 and a thermoplastic film material 16, bonded to the base 14 prevents the entry of saturated steam and the escape of hydrochloric acid and/or chlorine gas produced by the reacting indicator ink spots 12a, 12b and 12c through the covering films during the sterilization process and confine these corrosives within the absorbent, permeable base material 14.

Other choices for the impermeable covering material 10 include fluoroplastics, cellulosics, and polyamides.

Other choices for the thermoplastic film material 16 include polyethylene, acrylics and vinyls.

The sterility indicator of the instant invention by eliminating the release of corrosive reaction products produced by the reacting indicator inks enables use of the indicator in immediate contact with the goods to be sterilized.

Tests were made to determine the effectiveness of the impermeable covering film in preventing the escape of corrosive reaction products. Indicator strips with and without the impermeable covering films were placed face down on hospital type linen strips. The location of the indicator ink spot was marked on the cloth. The cloth was folded over the indicator strip and secured. Both groups of strips were autoclaved for 40 minutes at 250° F. in saturated steam to assure reproduction of time, temperature and saturated steam conditions used during sterilization of hospital garments. Upon removal of the strips from the autoclave, a Mullen tester was used to determine the breaking strength of the cloth. Two tests were made on each piece of cloth, one at the location of the indicator ink as marked on the cloth, the other at a point furthest away from the indicator ink spot. The cloth in the area under the indicator ink spot without the protective film covering showed an average loss of tensile strength of 66 percent. The cloth in the area under the indicator ink spot with the protective film showed a tensile strength slightly better than the average of the cloth away from the indicator spot (this result is attributed to variations in the tensile strength of the cloth).

The combined films 20 and 20a can be manufactured either by extruding melted thermoplastic film material 16 directly onto the impermeable covering film 10 or by combining a solid film of the thermoplastic film material to the impermeable covering 10 with another suitable adhesive 17, an example of which is epoxy resin.

In an alternate embodiment of the invention as shown in FIG. 4 the impermeable covering film may be bonded to the base 14 directly by means of a suitable adhesive 17, thereby eliminating the thermoplastic film layer 16.

For the indicator to function and undergo a color change in one or more of the respective indicator ink spots 12a, 12b and/or 12c saturated steam at predetermined time/temperature values must be present. Thus, if sufficient steam is not present during the sterilization process the indicator ink will not react to produce a color change even though the sterilization temperature has been reached thereby indicating a "dry" or insufficient sterilization of the goods, e.g. the presence of air in the autoclave.

The saturated steam while prevented from entering through the impermeable covering film reacts with the indicator ink spots 12a, 12b or 12c by being transmitted through the edge portions of the absorbent base material 14 sandwiched between the impermeable covering layers 20 and 20a. The hydrocloric acid and/or chlorine gas produced by the reacting indicator ink spots 12a, 12b and 12c is confined within the absorbent base material 14 provided the volume of the base material surrounding the indicator ink spots is large enough to absorb the volume of reactants produced.

While the required volume of absorbent base material necessary to contain the corrosive reaction products may be calculated given the base's permeability and absorbtion coefficients, and the volume of reaction products produced, a trial and error approach results in the most rapid method of selecting the thickness and width of a given base material for indicator ink spots of a given size. For example, a suitable thickness for a base of paperboard material is 0.020 inches, which allows the indicator width to be kept to a reasonable 0.625 inches for ink spots 0.1875 inch by approximately 1.0 inch.

The invention and its attendant advantages will be understood from the foregoing description and it will be apparent that changes may be made in the form, construction and arrangement of the parts of the invention without departing from the spirit and scope thereof, the arrangements hereinbefore described being merely by way of example. We do not wish to be restricted to the specific forms shown or uses mentioned except as defined in the accompanying claims.

We claim:

1. A sterility indicator device comprising:
   a. a base of absorbent material which is permeable to saturated steam;
   b. indicator means reactive to predetermined combinations of time, temperature and saturated steam mounted on one surface of said base, said indicator means being of the type which evolves corrosive gaseous reaction products upon reacting with saturated steam;
   c. a first gas impermeable, transparent covering film bonded by adhesive means to said one surface of said base and overlaying said indicator means;
   d. a second gas impermeable covering film bonded by adhesive means to another surface of said base such that said base and indicator means are interposed between said first and said second covering films, the edge portions of said base being exposed so that steam enters said base via said exposed edge portions, said steam moving through said base into contact with said indicator means to react with said indicator means, said indicator means being spaced from said exposed edge portions so that said steam must move through said base to contact said indicator means, said base and said first and second covering films preventing the corrosive gaseous reaction products evolved by said indicator means from escaping from the device, thereby forcing said corrosive gaseous products to be absorbed into said absorbent base; and
   e. said absorbent base having a gaseous absorption volume sufficient to absorb essentially all of said corrosive gaseous reaction products whereby essentially no corrosive gaseous reaction products escape from the indicator device but are contained within said indicator device so that materials being sterilized by the saturated steam will not be damaged by contact with said corrosive gaseous products.

2. The indicator of claim 1, wherein the base is comprised of paper.

3. The indicator of claim 1, in which said covering film is a film of material selected from the group consisting of polyester fluorplastics, cellulosics and polyamides.

4. The indicator of claim 1, wherein said adhesive means is comprised of polyethylene or epoxy resins.

5. The indicator of claim 1, wherein the indicator means is anhydrous chromium chloride.

6. The indicator of claim 5 comprising a plurality of indicator means, each of said means being visually responsive to different predetermined combinations of time, temperature and saturated steam conditions.

* * * * *